US00PP33562P2

(12) United States Plant Patent
Bacon

(10) Patent No.: US PP33,562 P2
(45) Date of Patent: Oct. 19, 2021

(54) APRICOT TREE NAMED 'SUAPRI15'

(50) Latin Name: *Prunus armeniaca*
Varietal Denomination: Suapri15

(71) Applicant: Sun World International, LLC, Bakersfield, CA (US)

(72) Inventor: Terry A. Bacon, Bakersfield, CA (US)

(73) Assignee: Sun World International, LLC, Bakersfield, CA (US)

( * ) Notice: Subject to any disclaimer, the term of this patent is extended or adjusted under 35 U.S.C. 154(b) by 0 days.

(21) Appl. No.: 17/204,214

(22) Filed: Mar. 17, 2021

(51) Int. Cl.
*A01H 5/08* (2018.01)
*A01H 6/74* (2018.01)

(52) U.S. Cl.
USPC ..... Plt./186

(58) Field of Classification Search
USPC ..... Plt./156, 186
See application file for complete search history.

*Primary Examiner* — Susan McCormick Ewoldt
*Assistant Examiner* — Karen M Redden
(74) *Attorney, Agent, or Firm* — Knobbe, Martens, Olson & Bear, LLP

(57) ABSTRACT

A new and distinct variety of apricot tree, *Prunus armeniaca* 'Suapri15', is characterized by having fruit that is medium sized, with dark orange flesh that ripens midseason. The fruit of the new variety 'Suapri15' also has firm flesh, a mildly sweet flavor with abundant aroma and a stone that has very weak adherence to the flesh.

1 Drawing Sheet

Latin name of the genus and species claimed: *Prunus armeniaca.*

Variety denomination: 'SUAPRI15'.

BACKGROUND AND SUMMARY OF THE INVENTION

This application relates to the discovery and asexual propagation of a new and distinct variety of apricot tree, *Prunus armeniaca* 'Suapri15'. The new variety was first originated by hybridization and identified in May 2011 by Terry A. Bacon as breeder number 'AP13141'.

The seed parent is 'Robada' (U.S. Plant Pat. No. 9,890), and the pollen parent is unknown (from a bulk pollen of unpatented breeding program selections). The parent varieties were first crossed in February 2008, the date of first sowing being February 2009 and the date of first flowering being February 2011. The new apricot variety 'Suapri15' was first asexually propagated by Terry A. Bacon near Wasco, Kern County, Calif. in February 2012 by dormant grafting.

The new variety 'Suapri15' is characterized by having fruit that is medium sized, with smooth skin and dark orange flesh that ripens midseason. The fruit of the new variety 'Suapri15' also has firm flesh, a mildly sweet flavor with abundant aroma and a stone that has very weak adherence to the flesh.

The new variety 'Suapri15' differs from its seed parent 'Robada' (U.S. Plant Pat. No. 9,890) in that the fruit of the new variety 'Suapri15' ripens about 3 days before that of 'Robada'. The skin of the fruit of the new variety 'Suarpi15' is smooth compared to bumpy skin for the fruit of 'Robada'. Further, the fruit of the new variety 'Suapri15' has a higher brix at 18% and higher Brix:Acid ratio at 23 compared to about 15% brix and a Brix:Acid ratio of 19 for 'Robada'.

The fruit of the new variety 'Suapri15' ripens about 7 days later than the fruit of 'Suaprinine' (U.S. Plant Pat. No. 16,507) and 12 days later than 'Poppy' (U.S. Plant Pat. No. 9,593). Further, the fruit of the new variety has a higher brix at 18% compared to 14% for 'Suaprinine' and 11% for 'Poppy'. The fruit of the new variety 'Suapri15' has 15% blush where exposed to sunlight compare to no blush for 'Poppy'.

The new variety 'Suapri15' has been shown to maintain its distinguishing characteristics through successive asexual propagations by, for example, cuttings and grafting.

BRIEF DESCRIPTION OF THE PHOTOGRAPH

The accompanying color photographic illustration shows typical specimens of the foliage and fruit of the apricot variety 'Suapri15'. The illustration shows the upper and lower surfaces of the leaves and exterior and sectional views of the fruit. The photographic illustration was taken shortly after the fruit was picked and the colors are as nearly true as is reasonably possible in a color representation of this type.

DETAILED DESCRIPTION

Throughout this specification, color names beginning with a small letter signify that the name of that color as used in common speech is aptly descriptive. Color names beginning with a capital letter designate values based upon The R.H.S. Colour Chart published by The Royal Horticultural Society, London, England, 1986.

The descriptive matter which follows pertains to three-year-old 'Suapri15' plants grown in the vicinity of Wasco, Kern County, Calif. during 2019 and is believed to apply to plants of the variety grown under similar conditions of soil and climate elsewhere.

TREE

General: (Measurements taken on three-year-old trees unless otherwise noted).

*Size.*—Medium: reaches a height of approximately 3 meters with normal pruning.

*Habit.*—Semi-upright.

*Vigor*.—Medium-strong. Top shoot growth of about 1 meter during the growing season.
*Productivity*.—Very productive.
*Distribution of flower buds*.—On spurs and on one-year old shoots.
*Degree of branching*.—Medium, branches readily.
*Fertility*.—Self-incompatible; requires pollinator.
*Hardiness*.—Hardy in all fruit growing areas of California. Winter chilling requirement is approximately 600 hours at or below 7.2° C.
*Disease resistance/susceptibility*.—Under close observation in Kern County, Calif., no particular plant/fruit disease resistance/susceptibility has been observed.
*Insect resistance/susceptibility*.—Under close observation in Kern County, Calif., no particular plant/fruit insect resistance/susceptibility has been observed.

Trunk: (Measurements taken at approximately 30 cm above soil line on mature tree).
*Diameter*.—Approximately 20 cm.
*Texture*.—Medium shaggy, increasing with age of tree.
*Trunk color*.—About Light Greyed-Green 198D with highlights of Medium Greyed-Red 182B, becoming darker with age.

Branches: (Measurements taken at approximately 90 cm above soil line).
*Size*.—Diameter approximately 11 cm.
*Texture*.—Medium shaggy, increasing with age.
*Color*.—About Light Grey 201D with highlights of about Medium Greyed-Red 182B, becoming darker with age.
*Lenticels*.—Present.
*Lenticels density*.—Plentiful, about 1-3/cm$^2$.
*Lenticels color*.—About Light Grey 201D.
*Lenticels dimensions*.—Length: approximately 5 mm. Width: approximately 1.2 mm.

One year old shoots: (Data taken in May at mid-point of current-season growth).
*Size*.—Medium, average diameter is approximately 5 mm.
*Topside color*.—About Dark Red-Purple 59A.
*Underside color*.—About Dark Red-Purple 59A.
*Internode length*.—Medium, approximately 20 mm.
*Lenticels color*.—About Light Grey 201D.
*Lenticels dimensions*.—Length: approximately 1 mm. Width: approximately 0.2 mm.
*Lenticels density*.—Plentiful, about 8/cm$^2$.
*Density of flower buds*.—Medium, two per node.
*Size of bud support*.—Medium, approximately 7.5 mm where shoot is 5 mm.
*Presence of anthocyanin coloration*.—Present.
*Anthocyanin coloration of apex during rapid growth* (*young shoot*).—Medium Red 53D coloration during rapid growth.

Vegetative buds: (Data taken in September at mid-point of current-season growth).
*Size*.—Approximately 2.5 mm wide×5 mm long.
*Shape*.—Ovoid.
*Color*.—About Dark Greyed-Purple 187A.

Flower buds: (Data taken in September at mid-point of current-season growth).
*Shape*.—Ovoid.
*Dimensions*.—Approximately 2 mm wide×3 mm long.
*Color*.—About Dark Greyed-Purple 187A.
*Ratio of flowering buds to vegetative buds*.—2 flower buds to 1 vegetative bud.

FOLIAGE

Leaves: (Data taken in May at mid-point of the current season growth).
*Average length*.—Medium; approximately 62 mm without petiole.
*Average width*.—Medium; approximately 67 mm.
*Length/width ratio*.—Very small; about 0.9:1.
*Shape*.—Circular.
*Color*.—Upper surface: About Dark Green 136A. Lower surface: About Medium Green 137A.
*Leaf blade*.—Intensity of green color of upper side: Medium.
*Angle at apex*.—Acute.
*Vein color*.—About Medium Yellow-Green 144A.
*Presence of red coloration on mid-vein on the lower side*.—Present.
*Surface texture*.—Smooth on both upper and lower surfaces.
*Leaf blade*.—length of tip: Medium, approximately 5 mm.
*Leaf blade tip*.—Slightly curved downwardly
*Incision of margins*.—Crenate.
*Undulation of margin*.—Weak.
*Profile in cross section*.—Moderately concave.

Petiole:
*Average length*.—Long, approximately 32 mm.
*Ratio of blade/length petiole*.—Medium, about 1.9:1.
*Thickness*.—Medium, approximately 2 mm.
*Color*.—About Dark Red-Purple 59A.
*Anthocyanin coloration of upper side*.—Strong.

Stipules:
*Number/leaf bud*.—Usually two.
*Typical length*.—Medium, approximately 11 mm.
*Color*.—About Dark Greyed-Orange 166A when dried.
*Persistence*.—Falls off.

Nectaries:
*Predominate number and arrangement*.—Ranges from 2-4, usually 3-4, alternating on petiole.
*Form*.—Globose.
*Size*.—Medium, Approximately 1.0 mm long×1.0 mm wide.
*Color*.—About Medium Greyed-Yellow 162A becoming Dark Greyed-Orange 166A over time.

FLOWERS

General:
*Flower form*.—Rosette.
*Flower diameter*.—Medium, approximately 28 mm.
*Flower aroma*.—Slight.
*Time of beginning of leaf bud burst*.—Medium, with bloom.
*Time of beginning of flowering*.—Medium for the San Joaquin Valley, Calif.
*Flower blooming period*.—First bloom: Approximately February 23 in Wasco, Calif. Full bloom: Approximately February 27 in Wasco, Calif.
*Location of first bloom*.—Tips of one-year old shoots.
*Location of full bloom*.—Central part of the tree canopy.
*Duration of bloom*.—Approximately 10 days.

Pedicels:
*Length*.—Approximately 3 mm.
*Width*.—Approximately 2 mm.
*Color*.—About Medium Green 138B.
Sepals:
*Number*.—5.
*Shape*.—Medium ovate.
*Length*.—Approximately 5 mm.
*Width*.—Approximately 3 mm.
*Color*.—About Medium Greyed-Purple 184A.
*Surface texture*.—Smooth.
*Positioning*.—Adpressed to petals.
Receptical:
*Depth*.—Medium, approximately 4 mm.
*Pubescence of inner surface*.—Absent.
*Pubescence of outer surface*.—Absent.
Stigma:
*Position relative to anthers*.—Below.
Petals:
*Number*.—5.
*Arrangement*.—Slightly overlapping.
*Shape*.—Circular.
*Color on lower side*.—About Light Red 54D.
*Surface texture*.—Smooth.
*Length*.—Approximately 12 mm.
*Width*.—Approximately 10 mm.
*Apex shape*.—Rounded.
*Base shape*.—Narrows at point of attachment.
*Undulation of margins*.—Medium.
*Frequency of flowers with double petals*.—None.
*Claw*.—Partially developed.
Pistil:
*Frequency of supplementary pistils*.—Few.
*Average length*.—Approximately 17 mm.
*Ovary diameter*.—Approximately 2 mm.
Ovary:
*Pubescence*.—Absent.
Stamens:
*Number*.—About 40.
*Average length*.—Variable, ranging from 7 mm to 10 mm.
*Filament color*.—About White 155A with highlights of Light Red 54D.
*Pollen color*.—About Dark Greyed-Orange 166C.
*Position compared to petals*.—At same level.
Anthers:
*Pollen*.—Present.

FRUIT

General: (Description taken at firm-mature near Wasco, Kern County, Calif.).
Ripening:
*Time of beginning of fruit ripening*.—Mid-season.
*Date of first pick*.—Approximately May 14.
*Date of last pick*.—Approximately May 24.
Size:
*Height*.—Tall, approximately 64 mm.
*Average weight*.—Medium, approximately 90 gm.
*Diameter lateral vie, suture sideways*.—Medium, approximately 55 mm.
*Diameter ventral view, facing suture*.—Medium, approximately 55 mm.
*Ratio height/ventral width*.—Medium, about 1.2:1.
*Ratio lateral wigtht/ventral width*.—Small, about 1:1.
Peduncle:
*Length of stem*.—Approximately 7 mm.
*Diameter of stem*.—Approximately 3 mm.
*Color of sent*.—About Light Green 139D.
Shape:
*Viewed from apex*.—Nearly circular.
*Lateral view, perpendicular to suture*.—Oblong.
*Ventral view, facing suture*.—Oblong.
*Symmetry in ventral view*.—Slightly asymmetric.
*Symmetry viewed from pistil end*.—Nearly symmetric.
*Shape of pistil end*.—Slightly depressed.
*Presence of mucro on pistil end*.—Occasionally present.
*Shape of apex*.—Rounded.
*Appearance of suture*.—Slightly sunken.
*Depth of stalk cavity*.—Medium, Approximately 8 mm.
*Width of stalk cavity*.—Medium, Approximately 7 mm.
Fruit skin:
*Thickness*.—Medium; typical of most varieties.
*Adherence to flesh*.—Medium.
*Flavor*.—Mildly tart.
*Surface texture*.—Smooth.
*Reticulation*.—Absent.
*Tendency to crack*.—Slight to none.
*Pubescence*.—Slightly present.
*Density of pubescence*.—Medium.
*Ground color*.—About Dark Orange 26A.
*Relative area of overcolor*.—Small, about 15%, more where exposed to sun.
*Overcolor hue*.—About Dark Red 42A.
*Pattern of overcolor*.—Solid flush.
*Intensity of overcolor*.—Medium.
Flesh:
*Ripens*.—Evenly.
*Color*.—About Dark Orange-Red 32A.
*Anthocyanin coloration of flesh next to skin*.—Absent.
*Anthocyanin coloration of flesh in central part of flesh*.—Absent.
*Anthocyanin coloration of flesh around stone*.—Absent.
*Flavor*.—Sweet-mild with abundant aroma.
*Texture*.—Medium-fine flesh.
*Firmness*.—Firm; typically 8 lb pressure at harvest.
*Sweetness*.—High; about 18% Brix at harvest.
*Acidity*.—Medium; 0.78% titratable acidity.
*Amount of fiber*.—Medium.
*Adherence to stone*.—Absent or very weak.
Fruit use: Fresh market.
Fruit shipping and keeping quality: Good.
Stone:
*Stone size*.—Size: Medium. Length: Approximately 27 mm. Diameter facing suture: Approximately 16 mm. Diameter lateral view: Approximately 24 mm. Weight: 2 gm when dried.
*Ratio weight of fruit/weight of stone*.—Large, about 45:1.
*Color*.—About Light Greyed-Orange 165C when dried.
*Anthocyanin coloration*.—Absent.
*Intensity of brown color*.—Medium.
*Position of maximum diameter*.—Middle.
*Shape from lateral view with suture sideways*.—Medium elliptic.
*Shape from in ventral view facing suture*.—Narrow elliptic.

*Shape from basal view*.—Medium elliptic.

*Base shape*.—Nearly straight.

*Apex shape*.—Slightly point at tip.

*Ridges*.—Rounded throughout.

*Outgrowing keel*.—Partially developed.

*Fibers*.—Not visible.

*Symmetry in lateral view*.—Symmetrical or slightly asymmetrical.

*Relief of surface*.—Slight-small grooves, mostly smooth.

*Width of stalk-end*.—Medium.

*Tendency to split*.—Low.

*Kernal bitterness*.—Medium bitterness.

What is claimed is:

1. A new and distinct variety of apricot tree as herein described and illustrated.

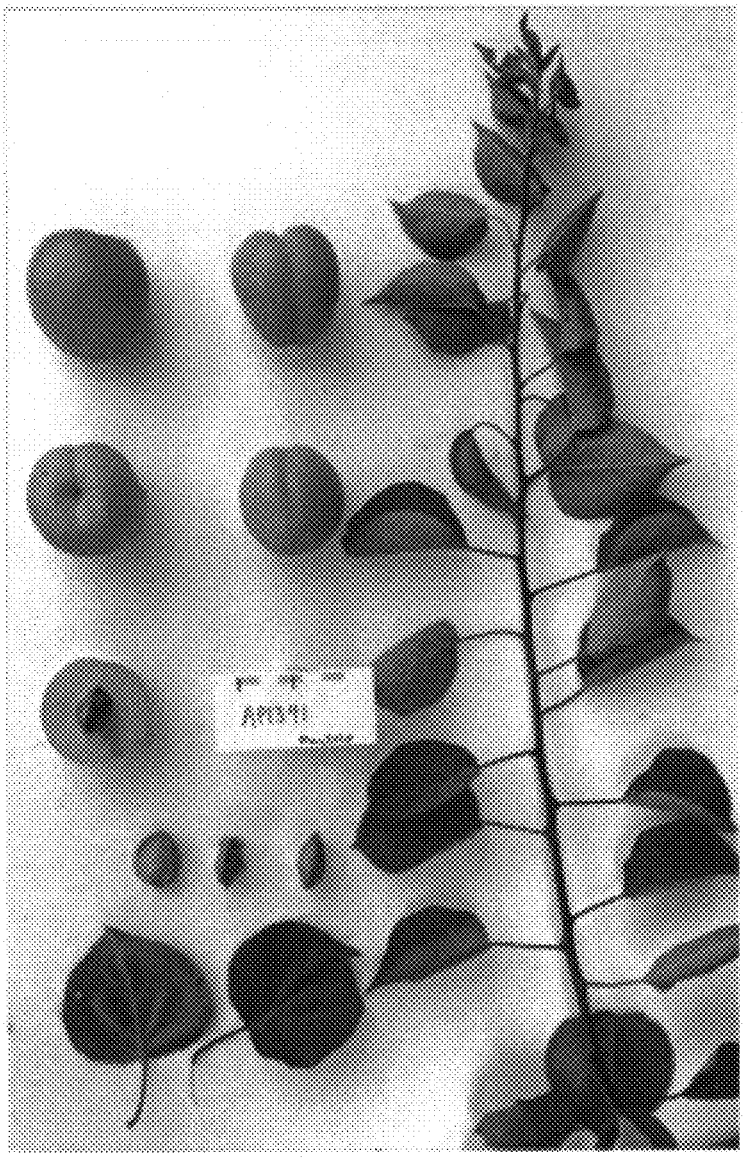

* * * * *